US011232176B1

(12) United States Patent
Leonardi (10) Patent No.: US 11,232,176 B1
(45) Date of Patent: Jan. 25, 2022

(54) COLLECTION, ARRANGEMENT, LINKAGE AND ALLOCATION OF LONGITUDINAL COST, REIMBURSEMENT AND CLINICAL DATA AT THE PATIENT ENCOUNTER LEVEL

(71) Applicant: SENTRY DATA SYSTEMS, INC., Deerfield Beach, FL (US)

(72) Inventor: Travis Leonardi, Deerfield Beach, FL (US)

(73) Assignee: SENTRY DATA SYSTEMS, INC., Deerfield Beach, FL (US)

( * ) Notice: Subject to any disclaimer, the term of this patent is extended or adjusted under 35 U.S.C. 154(b) by 1003 days.

(21) Appl. No.: 14/876,437

(22) Filed: Oct. 6, 2015

Related U.S. Application Data

(60) Provisional application No. 62/060,395, filed on Oct. 6, 2014.

(51) Int. Cl.
*G16H 10/60* (2018.01)
*G06F 19/00* (2018.01)

(52) U.S. Cl.
CPC ......... *G06F 19/3456* (2013.01); *G16H 10/60* (2018.01)

(58) Field of Classification Search
CPC .................. G16H 10/60; G06F 19/3456
See application file for complete search history.

(56) References Cited

U.S. PATENT DOCUMENTS

| 5,832,450 | A | * | 11/1998 | Myers | G06Q 50/24 |
| | | | | | 705/3 |
| 2011/0054935 | A1 | * | 3/2011 | Hardaway | G06F 19/328 |
| | | | | | 705/3 |
| 2012/0330677 | A1 | * | 12/2012 | Velimesis | G06Q 50/22 |
| | | | | | 705/2 |
| 2014/0324472 | A1 | * | 10/2014 | Delaney | G16H 10/60 |
| | | | | | 705/3 |
| 2014/0358578 | A1 | * | 12/2014 | Ptachcinski | G06Q 50/22 |
| | | | | | 705/2 |
| 2015/0039331 | A1 | * | 2/2015 | Longman | G06F 19/326 |
| | | | | | 705/2 |
| 2015/0278924 | A1 | | 10/2015 | Maurer | |

OTHER PUBLICATIONS

Sample 340B Policy & Procedures Manual, Feb. 2014, Apexus, pp. 1-18.

* cited by examiner

*Primary Examiner* — Evangeline Barr
(74) *Attorney, Agent, or Firm* — Loeb & Loeb LLP (57) ABSTRACT

The example embodiments may relate to systems, methods, apparatuses, devices, and computer readable media for collecting and presenting information at the patient encounter level. The example embodiments may include processing an encounter detail file associated with treatment a healthcare provider provided to a patient during a patient encounter, generating a linkage that links the encounter detail file with at least one other file associated with the patient encounter, and storing the linkage in a longitudinal patient administration record. The example embodiments may further include processing the longitudinal patient administration record to determine a metric and select an item based on the metric, and generating and communicating an order to a supplier for the selected item to cause delivery of the selected item to a desired location.

20 Claims, 4 Drawing Sheets

COLLECTION, ARRANGEMENT, LINKAGE AND ALLOCATION OF LONGITUDINAL COST, REIMBURSEMENT AND CLINICAL DATA AT THE PATIENT ENCOUNTER LEVEL

CROSS REFERENCE TO RELATED APPLICATIONS

This application claims the benefit of, and priority to, U.S. Prov. Appl. No. 62/060,395 filed Oct. 6, 2014, entitled "Collection, Arrangement, Linkage And Allocation Of Longitudinal Cost, Reimbursement And Clinical Data At The Patient Encounter Level," the entire content of which is incorporated herein by reference.

BACKGROUND

Field of the Invention

The invention relates to systems and methods for collecting and presenting information at the patient encounter level. Among other fields and applications, the invention has utility in facilitating management of health care providers.

Description of Related Art

Hospitals across the country are challenged with optimally managing their financial performance while simultaneously improving the quality of care and outcomes of their patient populations. Existing technologies do not satisfactorily address these issues.

SUMMARY

The following presents a simplified summary of the present disclosure in order to provide a basic understanding of some aspects of the disclosure. This summary is not an extensive overview of the disclosure. It is not intended to identify key or critical elements of the disclosure or to delineate the scope of the disclosure. The following summary merely presents some concepts of the disclosure in a simplified form as a prelude to the more detailed description provided below.

The example embodiments may relate to systems, methods, apparatuses, devices, and computer readable media for collecting and presenting information at the patient encounter level. The example embodiments may include processing an encounter detail file associated with treatment a healthcare provider provided to a patient during a patient encounter, generating a linkage that links the encounter detail file with at least one other file associated with the patient encounter, and storing the linkage in a longitudinal patient administration record. The example embodiments may further include processing the longitudinal patient administration record to determine a metric and select an item based on the metric, and generating and communicating an order to a supplier for the selected item to cause delivery of the selected item to a desired location.

BRIEF DESCRIPTION OF THE DRAWINGS

The invention may be better understood by references to the detailed description when considered in connection with the accompanying drawings. The components in the figures are not necessarily to scale, emphasis instead being placed upon illustrating the principles of the invention. In the figures, like reference numerals designate corresponding parts throughout the different views.

Persons of ordinary skill in the art will appreciate that elements in the figures are illustrated for simplicity and clarity so not all connections and options have been shown to avoid obscuring the inventive aspects. For example, common but well-understood elements that are useful or necessary in a commercially feasible embodiment are not often depicted in order to facilitate a less obstructed view of these various embodiments of the present disclosure. It will be further appreciated that certain actions and/or steps may be described or depicted in a particular order of occurrence while those skilled in the art will understand that such specificity with respect to sequence is not actually required. It will also be understood that the terms and expressions used herein are to be defined with respect to their corresponding respective areas of inquiry and study except where specific meanings have otherwise been set forth herein.

DETAILED DESCRIPTION

The present invention now will be described more fully with reference to the accompanying drawings, which form a part hereof, and which show, by way of illustration, specific exemplary embodiments by which the invention may be practiced. These illustrations and exemplary embodiments are presented with the understanding that the present disclosure is an exemplification of the principles of one or more inventions and is not intended to limit any one of the inventions to the embodiments illustrated. The invention may be embodied in many different forms and should not be construed as limited to the embodiments set forth herein; rather, these embodiments are provided so that this disclosure will be thorough and complete, and will fully convey the scope of the invention to those skilled in the art. Among other things, the present invention may be embodied as methods, systems, computer readable media, apparatuses, or devices. Accordingly, the present invention may take the form of an entirely hardware embodiment, an entirely software embodiment, or an embodiment combining software and hardware aspects. The following detailed description is, therefore, not to be taken in a limiting sense.

Current technologies fail to identify and allocate both total provider cost of care and profitability at a patient encounter level, in near real-time, using multiple bi-directional electronic internal hospital, external third party suppliers/partners, and patient medical records data. Moreover, existing technologies do not collect a combination of claims, procurement and detailed utilization data at the transactional level and link it to patient encounters to form, for example, a comprehensive and accurate longitudinal view (e.g., "over time" view) of a patient's care. Therefore, identifying cost savings and revenue enhancement opportunities and quality of care improvements, may either not be achieved or in some cases may only be completed through labor intensive manual and/or estimation methodologies that typically contain unacceptable margins of error.

To overcome these and other deficiencies, the example embodiments automatically collect, arrange, link and allocate operational, clinical and financial data at the patient encounter level. The example embodiments assist hospitals and other healthcare providers to better manage their organization through the collection, integration and allocation of internal and external cost, reimbursement and clinical information. The example embodiments may provide hospitals or other healthcare provider organization access to patient and related data from a variety of existing internal and external patient, financial and clinical systems. The example embodiments connect this data and allocate it to the patient encounter level to support a variety of operational, financial and clinical analytics. The example embodiments further longitudinally organize this data by patient.

The example embodiments also facilitate health care providers' compliance with recent healthcare reforms at the national and local levels. Providers are increasingly reimbursed by health insurance organizations (public and private) based upon performance objectives and improvements in the quality of patient care and outcomes. In this changing reimbursement environment, the example embodiments make it easier for a hospital or other provider to understand the financial impact of these reimbursement models by providing healthcare data that connects costs, revenues and clinical information at the patient encounter level. The example embodiments may align internal and external data sources and make them accessible for analytical purposes that support identification of cost, revenue, profitability and quality of care outliers.

Figure 1:
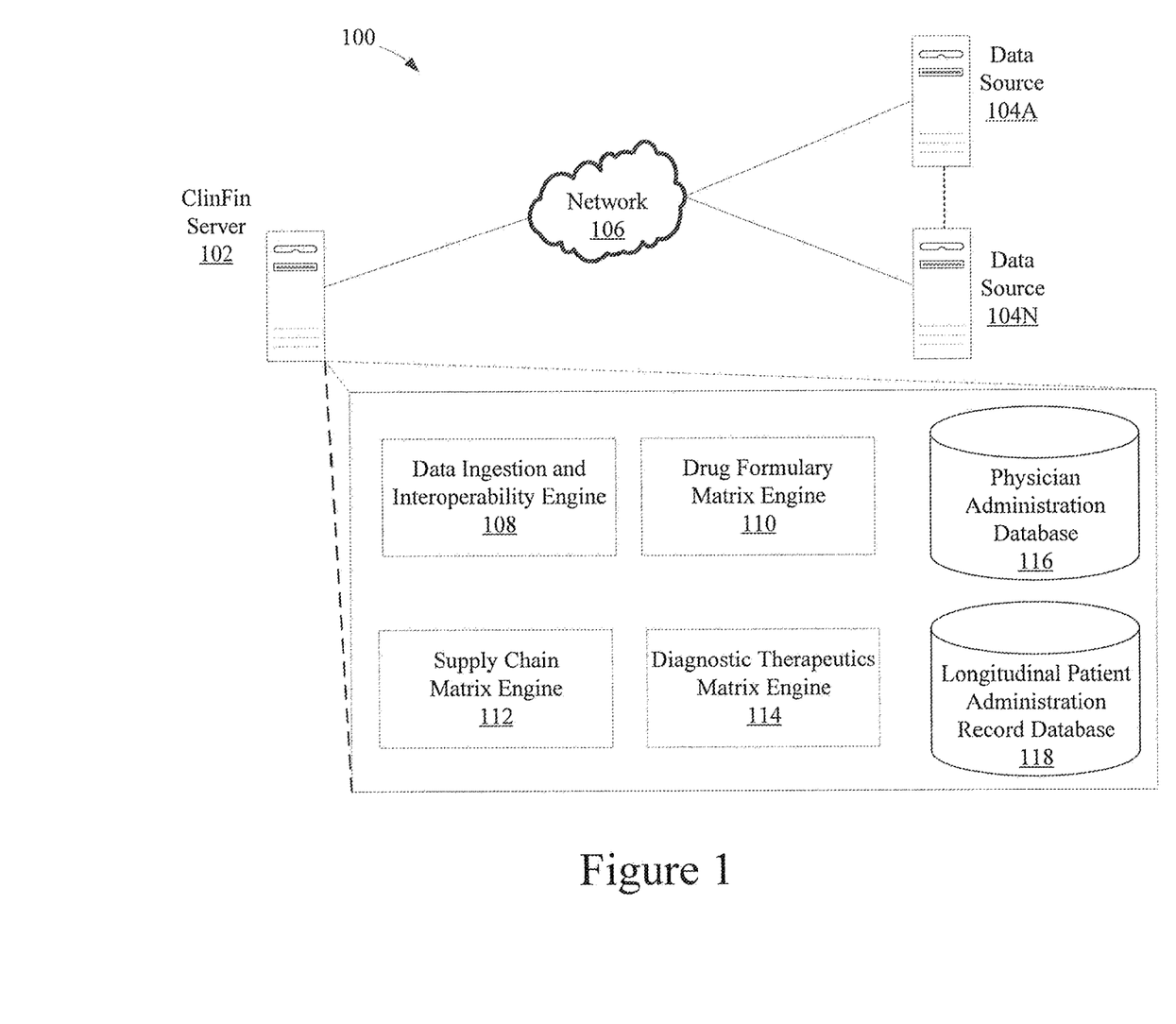
FIG. 1 illustrates a system in accordance with example embodiments.

FIG. 1 illustrates a system 100 in accordance with example embodiments. The system 100 may provide for linking of actual cost of care to a patient encounter. A patient encounter may be defined as the combination of a distinct patient, a continuous date-of-service with an admission and discharge event, a location(s)-of-service, and type of service. For example, a patient is admitted to the emergency room on the morning of day 1 and receives healthcare services (e.g., diagnostic radiology, lab, pharmacy, etc.) from one or more clinicians (e.g., doctors, nurses, nurse practitioners, allied staff, etc.). Later in the afternoon on day 1, the patient is transferred to an inpatient room in the hospital. The patient is given additional healthcare services (e.g., surgery, pharmacy, labs, etc.) and is subsequently discharged to home on day 4. In this example, the patient encounter was 4 days at 2 different hospital locations and involved the receipt of multiple healthcare services administered by multiple service providers. Another example of a patient encounter is treatment for a broken bone, which may include initial care (e.g., diagnosing the break, treating the break, and follow up visits). A further example of a patient encounter may be ongoing treatment for a disease requiring care over a period of time (e.g., diagnosing the disease and treating the disease over time).

Cost of caring for a patient may be based on a number of factors, including costs for supplies, medications, and labor. The example system 100 may collect, arrange, link, and allocate operational, clinical, and financial data for each patient encounter.

As depicted, system 100 may include a clinical financial (ClinFin) server 102 communicatively coupled to one or more data source servers 104A-N via network 106. The ClinFin server 102 may be an integrated technology platform that collects, arranges, links, and allocates operational, financial and clinical data at the patient encounter level. Data source servers 104A-N may communicate data to ClinFin server 102 about expenses incurred by a hospital or other health care provider during treatment of its patients. Types of data sources may include healthcare providers, wholesalers, distributors, suppliers, pharmacies, and the like. The data may include information on expenditures for medications or supplies purchased by the hospital, labor charges, real estate charges, and the like.

The ClinFin server 102 may include a number of engines 108, 110, 112, and 114 for processing data. Each engine described herein may be a discrete piece of hardware hard coded to perform the functions described herein. In other examples, the functions of an engine may be implemented in software as computer readable instructions stored in memory whereby execution of the computer readable instructions by at least one processor cause the at least one processor, or at least one computer, server, or other device, to perform the functions described herein. In yet other examples, any of the engines and functions described herein may be implemented as discrete pieces of hardware and others may be implemented in software. In other examples, an engine may include at least one processor and at least one memory storing computer executable instructions that, when executed by the at least one processor, cause the at least one processor, computer, server, or other device, to perform the functions described herein. In further examples, some functions performed by an engine may be implemented as one or more discrete pieces of hardware and other functions may be implemented in software.

In an example, a Data Ingestion and Interoperability Engine (DIIE) 108 may receive and process disparate operational, financial and clinical data files from hospitals and their operational and financial partners. The DIIE 108 may automatically import, parse, and process data files arriving in many different formats including financial/supply chain data standards (e.g., X.12), clinical data standards (e.g., HL7) and numerous technical data standards (e.g., Flat file, ODBC, XML, etc.). In addition to accepting a multitude of data formats, the DIIE 108 may be configured to account for a hospital's unique data definitions and anomalies.

The Drug Formulary Matrix Engine (DFME) 110 may connect and allocate a patient's drug utilization to the drug's purchase and cost information. The DFME 110 may break down a hospital's Charge Master (CM) into discrete drug formulary matrices that are identified by one or more National Drug Codes (NDC), Charge Description Master (CDM) codes, and a Units of Issuance (UOI) to CDM ratios. The Charge Master may contain detailed information on how services performed on patients are to be recorded and subsequently priced on a patient bill. In an example, the DFME 110 may utilize some or all of the following data feeds and drug identification numbers to accomplish its purpose:

Longitudinal Administration Record (LAR);
Physician Administration Database (PAD);
Charge Description Master (CDM);
Drug Purchase Orders (DPO);
Drug Purchase Invoices (DPI);
Patient Financial Charges (PFC);
Patient Drug Dispensations (PDD); and
National Drug Codes (NDC).

The LAR may be a database record of patient medical histories including diagnoses, treatments, service locations, service dates, service providers and related financial, clinical and demographic information. The PAD may be a database record of physicians including credentialing information, hospital admitting privileges and related demographic, educational and practice information. The CDM may be a code and description associated with at least some or all financial charges for billable and non-billable healthcare services. The DPO may be a record of drugs ordered by the hospital for utilization in Inpatient and Outpatient care delivery settings. The DPI may be a record of the amounts owed by the hospital for the drugs delivered as a result of the DPO. The PFC may be a record of some or all detailed charges for a patient associated with the services provided during an encounter. The PDD may be a record of the drugs that were administered to a patient during the course of a patient encounter. The NDC may be an 11 digit code assigned by the Food and Drug Administration and the drug manufacturer/labeler for a drug approved by the FDA.

In an example, a hospital may electronically send a purchase order to a wholesaler for purchasing one or more pharmaceuticals and may also send a copy of the purchase order to the ClinFin server 102. The wholesaler may respond with an invoice for the ordered pharmaceuticals and may also send a copy of the invoice to the ClinFin server 102. The wholesaler may also send a shipping notice to the hospital for the ordered pharmaceuticals and may also send a copy of the shipping notice to the ClinFin server 102 for reconciling the invoice with what was actually shipped.

In order to accurately associate a drug purchase and cost information to a drug dispensed to a patient during the course of an inpatient or outpatient encounter, the DFME 110 may automatically map a drug purchase and cost information to a dispensed drug. In some instances, hospital pharmacy staff may assist with the mapping. In an example, a hospital may have its own identifiers for a drug, and the DFME 110 may map a hospital specific identifier to the NDC of the drug manufacturer. For generic drugs, the DFME 110 may use a first-in, first-out (FIFO) method to reconcile purchased drugs to dispensed drugs. In some instances, a hospital may have a medicine cabinet having loose pills of equivalent medications supplied by two or more different drug manufacturers. Under the FIFO method, the DFME 110 may assume that a first of the equivalent drugs received by the hospital is the first drug dispensed by its staff, regardless of which one of the equivalent drugs was actually dispensed.

The Supply Chain Matrix Engine (SCME) 112 may link chargeable medical and surgical supply costs to a patient encounter. The SCME 112 may break down a hospital's Item Master (IM) and Charge Master (CM) into discrete medical/surgical supply formulary matrices. Together with other sources of information, these matrices reveal unit costs for supplies that are then allocated back to an individual patient's utilization of services contained in the patient's LAR.

The SCME 112 may utilize the following data feeds and supply chain identification numbers in order to accurately associate chargeable medical/surgical cost information to a patient during the course of an Inpatient or Outpatient encounter:

LAR;
PAD;
Item Master (IM);
Hospital Purchases (HP); and
Patient Financial Charges (PFC).

The LAR and PAD are defined above. The IM may be a database that identifies some or all products and services purchased by the hospital and that may be billable to a patient or their health insurance plan. For example, an Item Master may contain detailed information on products and their associated costs for items that are purchased by an organization for treating patients. The HP may be a record of some or all medical and surgical supply purchases made by the hospital. The PFC may be a record of some or all detailed charges for a patient associated with the services provided during an encounter.

Figure 2:
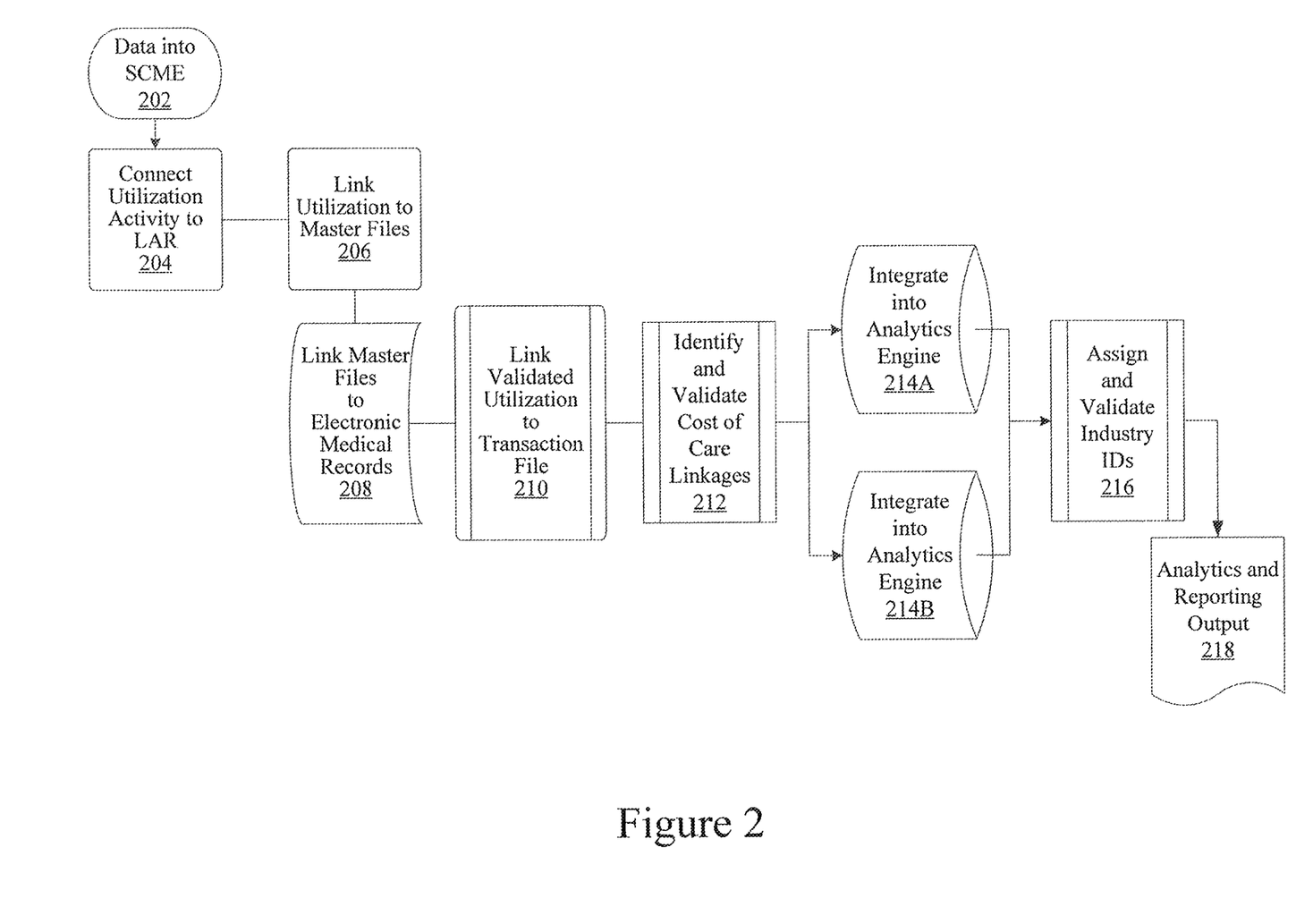
FIG. 2 illustrates a flow diagram of a process for creating a supply chain matrix in accordance to example embodiments.
Figure 3:
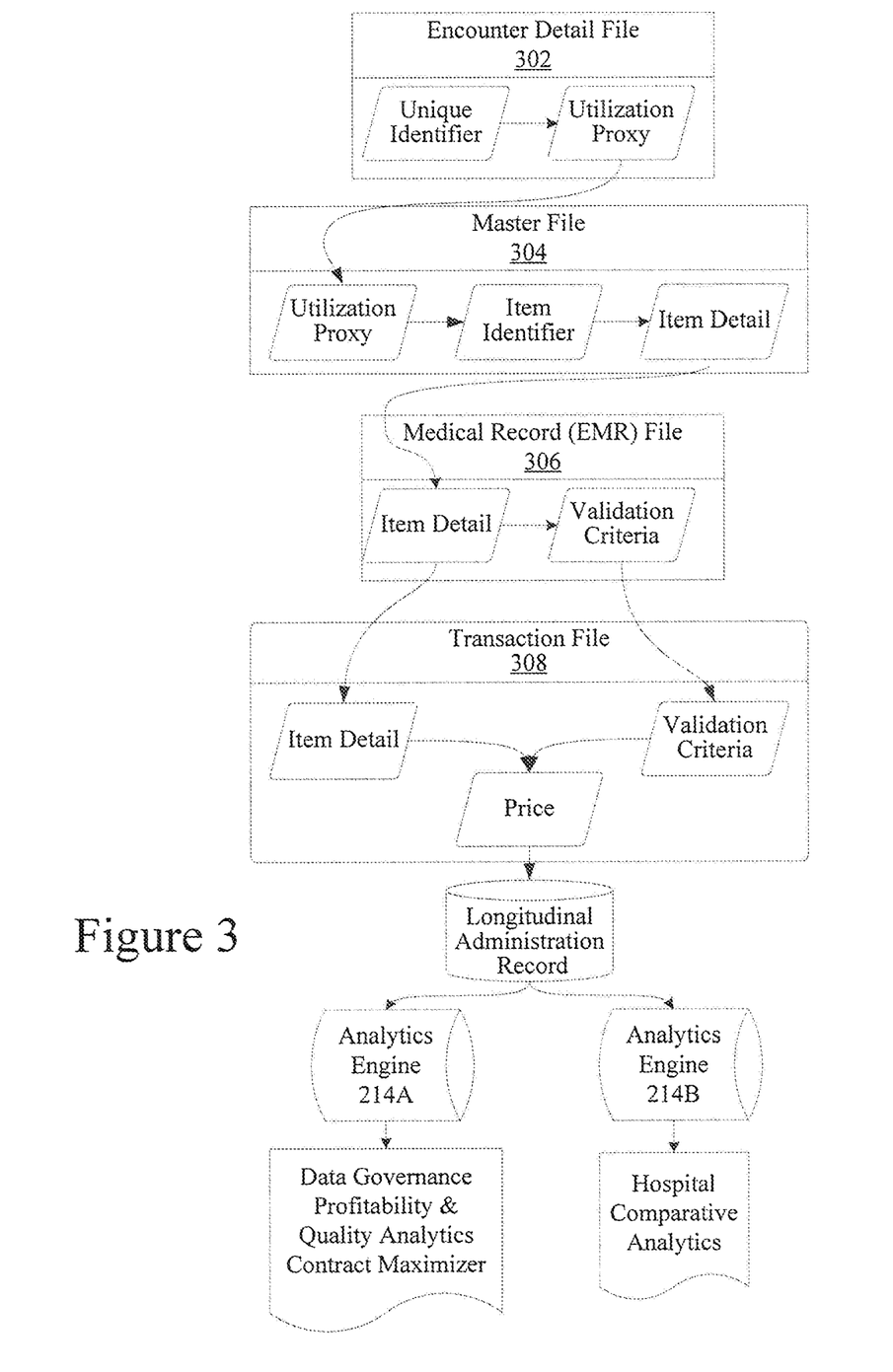
FIG. 3 illustrates examples of linkages created between files in accordance to example embodiments.

FIG. 2 illustrates a flow diagram of a process for creating a supply chain matrix and FIG. 3 illustrates examples of linkages created between files in accordance with example embodiments. At 202, the SCME 112 may import data a hospital or health system's clinical, operational, and financial data. For example, at least one processor of the SCME 112 may execute computer executable instructions to process data received from one or more data source servers 104A-N. At 204, the SCME 112 may connect utilization activity to an LAR. In an example, the SCME 112 may receive and process an encounter detail file having a patient identifier. The encounter detail file may also include clinical, operational, and financial data associated with a particular patient encounter. The SCME 112 may search the LAR database 118 using the patient identifier attempting to retrieve an existing LAR. For example, at least one processor of the SCME 112 may execute computer executable instructions to query the LAR database 118 attempting to retrieve an LAR. If none are associated with the patient identifier, the SCME 112 may create a new LAR for that patient encounter.

At 206, the SCME 112 may link utilization to master files. A master file may be an index file containing elements of cost and revenue data and may be used by the hospital to drive specific purchasing, charging and accounting functions. Master files for hospitals are typically maintained by separate systems that are not integrated with each other or with the medical record, and are typically not kept in synchronicity with one another. Charge masters and item masters are examples of master files. In conventional systems, an item purchased for a patient may be listed in an Item Master file, but a corresponding record may not have been added to a Charge Master file. In this scenario it becomes virtually impossible for the hospital to bill the patient for the use of that item during the course of the patient's care. This example is akin to a retail store having to do a price check for an item that is on their shelf but not ringing up correctly at the check-out register—however, it happens thousands of times each year at hospitals all over the country and they do not have a mechanism like a sales clerk who can quickly and easily obtain the correct information and override the system to accurately capture the utilization activity. The SCME 112 may update one or master files to indicate that a particular item (e.g., supply and/or drug) specified in the encounter detail file was utilized in a particular patient encounter. As used herein, the term item may encompass a supply item, a drug item, or both.

At 208, the SCME 112 may link master files to electronic medical records. An electronic medical record may be documentation in an electronic database of the care that a patient has received along with associated information on the reasons for the provision of care and their progression through the care process (e.g., symptoms, diagnostic test results, clinical diagnoses, etc.). To perform the linking, the SCME 112 may search a database of medical record files to identify one or master files having an item detail in common with a particular medical record. An item detail may be any number of attributes associated with an item or items that would differentiate it from other items in a Master File. Examples of an item detail include a catalog number, a description of the item, an identifier of the item assigned by its manufacturer, and the like.

At 210, the SCME 112 may link validated utilization to a transaction file. A transaction file may be a detailed receipt of one or more items an organization has bought for use in caring for patients and held in inventory for future delivery of care. Typically a transaction file may contain a specific item identifier and classification details as well as details on purchase price and alignment to established contracts that the hospital may have with its various suppliers and group purchasing organizations. However, due to the variations in hospital materials management information systems, some details—such as industry classification and contract alignment that are valuable in ensuring appropriate pricing and ability to benchmark meaningfully—may be omitted or housed in separate systems. Therefore, additional linkages, assignments, and validations such as those subsequently described below may be provided to enable more robust analytic capabilities and capture full savings benefit. To perform the linking, the SCME 112 may search a database of transaction files to identify one or transaction files having an item detail in common with a particular medical record.

At 212, the SCME 112 may identify and validate cost of care linkages. For example, the SCME 112 may validate cost of care linkages by applying validation criteria. In an example, validation criteria may be a set of common data elements existing in multiple files that are compared across files to ensure accuracy of the linkages. Examples of validation criteria include, but are not limited to, unique patient identifiers, facility codes, item catalogue numbers, etc.

At 214A-B, the SCME 112 may integrate both raw financial and operational data, cleansed data from the LAR, and publicly available data such as case mix and Medicare cost report data into one or more specially designed analytics engines for the purpose of performing both internal variability, quality, and profitability analysis as well as external comparative analysis and benchmarking. At 216, the SCME 112 may assign and validate industry identifiers. At 218, the SCME 112 may output analytics and reports.

FIG. 3 illustrates example linkages created by the process of FIG. 2. In an example, an encounter detail file 302 may link a unique identifier and a utilization proxy. The encounter detail file 302 may include data pertaining to specific actions taken to provide care to the patient during a particular encounter. This file may be obtained directly from an electronic medical record, or may be created by combining related data on an encounter from several disparate data sources within the hospital. The encounter detail file 302 may contain various fields related to care services performed and their associated charge activity—similar in concept to a detailed line-item receipt for items purchased at a store, or a detailed invoice for services performed by a tradesperson. A unique identifier may be an attribute that identifies a unique patient and associated episode of care. Examples of a unique identifier may include a visit number corresponding to a particular patient encounter, a patient identifier, a patient's social security number, a patient name, a patient's medical record number, and the like. A utilization proxy may be a data element within file 302 that serves as an indicator that a service was performed or a product administered during a particular patient encounter. Examples of a utilization proxy may include a charge code or a physician order. To create a linkage, the SCME 112 may retrieve the utilization proxy from file 302 and search a master file database for a master file 304 having the same utilization proxy. For example, the SCME 112 retrieve a master file 304 having the same charge code as in the encounter detail file 302. The master file 304 having the same utilization proxy may be linked to the encounter detail file 302.

The master file 304 may link the utilization proxy to an item identifier and an item detail. An item identifier may be a code used by a manufacturer to identify an item. An NDC is an example of an item identifier for a drug. A number, name, or alphanumeric sequence a manufacturer assigns to a product or device is another example of an item identifier. The SCME 112 may retrieve the item detail from file 304 and search a medical record database for a medical record file 306 having the same item detail for linking file 304 to file 306, signifying that file 304 and record 306 correspond to the same patent encounter. In an example, an item detail may be a catalog number and the SCME 112 may retrieve a medical record file 306 having the same catalog number as the master file 304. In some examples, the medical record may include validation criteria. Validation criteria may be a set of common data elements existing in multiple files that are compared across files to ensure accuracy of the linkages. Examples of validation criteria include, but are not limited to, unique patient identifiers, facility codes, item catalogue numbers, etc.

The SCME 112 may also use the item detail retrieved from file 304 and search a transaction file database for a transaction file 308 having the same item detail for linking file 304, file 306, and file 308. Continuing the above example where the item detail is a catalog number, the SCME 112 may retrieve a transaction file 308 having the same catalog number as the master file 304 and the medical record file 306. A transaction file 308 may include a price for a supply (e.g., medical device, etc.) or drug used to treat a patient, as well as a labor charge associated therewith. It is noted that multiple encounter detail files 302 may be associated with a single patient encounter, as multiple items may be used to treat a patient and/or a patient encounter may occur over a length of time and involve treatment in various locations of a hospital. The SCME 112 may thus identify and link each transaction file with an encounter detail file 302 corresponding to a single patient encounter. When multiple items are used to treat a patient, the SCME 112 may add prices for each supply (e.g., medical device, etc.), drug, and labor charge from each transaction file linked to a particular patient encounter to determine a total cost of care for a particular patient encounter. The SCME 112 may store the total cost of care in the LAR.

The SCME 112 may also generate and store a linkage in a Longitudinal Patient Administration Record (LAR) database 18 indicating a relationship between some or all of the encounter detail file 302, the master file 304, the medical record 306, and the transaction file 308 in the patient's LAR, signifying that those files correspond to a particular patient encounter. In an example, the linkage may be the utilization proxy and the item detail corresponding to a particular patient encounter such that the SCME 112 may utilize the linkage to retrieve each of the encounter detail file 302, the master file 304, the medical record 306, and the transaction file 308 for that patient encounter. In another example, the linkage may be unique identifiers for each of the encounter detail file 302, the master file 304, the medical record file 306, and the transaction file 308 corresponding to a particular patient encounter. In some examples, it is noted that multiple ones of files 302, 304, 306, and 308 may be linked to a particular patient encounter.

With reference again to FIG. 1, the LAR database 118 may be a relational database that stores systematic documentation of a single patient's medical history and care across time in an LAR associated with each patient. DIIE engine 108 may populate the LAR database 118 with encounter level data retrieved from an encounter detail file 302 that is received from hospital and financial data (e.g., costs, revenues, etc.). The DIIE engine 108 may receive the hospital and financial data from a hospital via supply chain, pharmacy, payers and other external partner organizations that support various operational, financial and clinical aspects of the hospital.

For example, the DIIE engine 108 may receive a data feed from a data source (e.g., a hospital server, a pharmacy server, a supplier server, etc.), wherein the data feed includes an encounter detail file 302 having a unique identifier. In an example, at least one processor of the SCME 112 may execute computer executable instructions to process a data feed received from one or more data source servers 104A-N. The DIIE engine 108 may retrieve from the encounter detail file 302 encounter data that includes the unique identifier, and describes an event and time/date stamp when the event occurred. In an example, an event may be that a clinician provided a patient a particular item (e.g., drug or product) during treatment. The DIIE engine 108 may utilize the unique identifier to determine whether the patient has an existing LAR. In an example, the DIIE engine 108 may assign each patient a LAR in the LAR database 118. Each LAR may include information for uniquely identifying a patient (e.g., name, address, social security number, patient number, etc.), a code or other identifier of an ailment or disease being treated, one or more event entries describing treatments the patient has received from the hospital or other activities associated with caring for the patient, and a date and time stamp corresponding to each event entry.

If a patient already has an LAR, the DIIE engine 108 may retrieve the existing LAR. If not, the DIIE engine 108 may create a new LAR for the patient. The DIIE engine 108 may update the LAR with the received event and time/date stamp corresponding to a particular patient encounter. Examples of event entries include arrival at an emergency room, admission to the hospital, assignment to a particular room, surgery by a particular doctor, and discharge of the patient. Each of the event entries may be date and time stamped to indicate when each occurred.

With reference again to FIG. 3, analytics engines of the ClinFin server 102 may process the patient's LAR, alone or in aggregate with other patient's LARs, for improving patient care and hospital performance. For example, analytics engine 214A may process one or more LARs attempting to improve or maximize both quality of care and hospital profitability. The analytics engine 214A may, for example, process the LARs to determine how well the healthcare provider is leveraging its existing contracts with suppliers. For example, the provider may enter into agreements to purchase drugs and/or supply items from a particular supplier at a price that is better than retail or wholesale. The analytics engine 214A may process the LARs to determine if those drugs and/or supply items are being bought from non-approved suppliers outside of the contract or if the provider is being charged by the supplier a price that exceeds the contract price. In another example, analytics engine 214B may process the LARs for comparing a hospital to other hospitals (e.g., peer hospitals). The analytics engine 214B may determine an aggregated metric (e.g., average total cost of care) for a first provider in treating its patients assigned a particular diagnosis code and determine an aggregated metric (e.g., average total cost of care) for peer providers in treating patients for the same diagnosis code. The analytics engine 214B may provide performance information to an administrator of the hospital for assessing relative performance.

With reference again to FIG. 1, the Diagnostic Therapeutics Matrix Engine (DTME) 114 may identify the drugs by National Drug Code (NDC) that are commonly prescribed for patient conditions (On-Label and Off-Label Uses) by disease and illness based upon the patient's primary and/or secondary diagnostic code(s) as defined by the International Classification of Diseases 9 and 10. For example, at least one processor of the DTME 114 may execute computer executable instructions for identifying the drugs by NDC. The DTME 114 may utilize the following data feeds to connect clinical diagnoses with drug therapies to a patient's LAR:
  LAR;
  ICD-9 and ICD-10 Codes; and
  National Drug Codes—Food and Drug Administration, Labelers The LAR is defined above. ICD-9 and ICD-10 Codes are diagnostic and procedure codes created by the World Health Organization and are used to classify the disease state of a patient during a patient encounter.

The Physician Administration Database (PAD) database 116 may be a relational database that stores systematic historical patient records of care for a single physician across time. DIIE 108 may populate the PAD database 116 with patient encounter level data received from a hospital or other health care provider.

In a further example, the LAR may provide information allocating labor costs to a patient encounter. The ClinFin server 102 may update a patient's LAR with time/date stamps for tracking a patient's movement through a hospital and treatments/supplies provided to the patient. In an example, a patient may arrive at an emergency room for treatment. Via information provided by the hospital employee, the ClinFin server 102 may determine that the patient has an existing LAR in the LAR database 118 or may generate a new LAR for the patient. The ClinFin server 102 may store a time/date stamp in the patient's LAR based on when the patient arrived and create an event entry (e.g., patient arrived) in the LAR associated with the time/date stamp. The event entry may identify what happened or what treatment was administered to the patient, and any labor associated with each entry (e.g., nurse administered medication and attended to patient for 10 minutes, name of nurse, and nurse's salary). Continuing the example, the ClinFin server 102 may then store a time/date stamp in the patient's LAR when the patient is admitted and a corresponding event log (e.g., patient admitted). The ClinFin server 102 may continue to update the patient's LAR with time/date stamps and event entries while under the hospital's care, and assign labor charges to each event entry based on the treatment and/or care provided. Another example of an event entry is a time stamp of 10:30 am to indicate when a patient was given a particular drug, an identifier of the drug (e.g., the NDC of the drug), amount of the drug given (e.g., 2 pills), and the cost of the drug (e.g., $25 for two pills). A further event entry example is a time stamp of 10:31 am, an identifier of a product used to treat the patient (e.g., an identifier of a splint, syringe, etc.), a quantity of the product used (e.g., one splint), and a cost the provider paid for the product (e.g., $50 per splint).

The ClinFin server 102 may also update event entries in the patient's LAR indicating the amount of money a patient, or the patient's insurance company, has paid for a particular treatment, drug, supply item, and the like. For example, the ClinFin server 102 may receive information from payment data sources (e.g., insurance payments, co-pays, patient payments, etc.) and a patient identifier to associate how much money a hospital received from the patient for a particular encounter. The ClinFin server 102 may associate payments with a particular patient encounter or particular event entries of the encounter. In example, the ClinFin server 102 may receive payment information from a payment data source providing payment of a fixed amount for treatment of a particular ailment (e.g., $1,500 to treat a patient for a broken arm). In some instances, the payment information may indicate payments for particular services. For example, the payment information may indicate that a first amount is paid for labor charges, a second amount is paid for supplies, a third amount is for laboratory services (e.g., x-rays), and a fourth amount is for medications. The ClinFin server 102 may update a patient's LAR to associate received payments with particular event entries.

The patient's LAR may thus serve as a record for identifying labor costs, pharmaceutical costs, and supply costs to treat a patient, and revenue the hospital received from a patient and/or insurance company for a particular patient encounter. Advantageously, the LARs may permit a hospital to know how much revenue it has received relative to its costs on an encounter by encounter basis.

The ClinFin server 102 may use patient LARs to monitor how variability on a patient encounter by encounter basis impacts clinical patient outcomes and financial outcomes for a health care provider that provided the treatment. Three examples discussed in further detail below include creating an audit trail for monitoring compliance with a drug discount program, monitoring compliance with supply items and/or drugs that have been approved for treatment of patients, and determining how variability in utilization of supplies, drugs, and impacts clinical and financial outcomes.

For example, the ClinFin server 102 may process patient LARs to create an audit trail for determining whether a health care provider is leveraging its benefits under a drug discount program, such as the U.S. federal government's 340B program. The U.S. federal government provides a 340B Drug Pricing Program that enables certain eligible healthcare organizations, referred to as Covered Entities (CEs), to receive discounts on drug prices. The 340B program is designed to ease the financial burden on institutions that disproportionately serve patients who are unable to pay for services they receive. CEs may be nonprofit health care organizations that meet certain Federal designations or receive funding from specific Federal programs that can purchase discounted drugs through the 340B Program. Examples of CEs include Disproportionate Share Hospitals (DSH), Sole Community Hospitals (SCH), Rural Referral Centers (RRC), Critical Access Hospitals (CAH), Children's Hospitals, Free Standing Cancer Centers, Community Health Centers (CHC), and Federally Qualified Health Centers (FQHC).

The 340B program reduces the cost of goods (typically medications) for eligible Outpatient (OP) areas of a hospital. These price reductions typically result in savings on eligible OP pharmaceutical purchases. In some instances, a CE may contract with a pharmacy (contract pharmacy or CP), which dispenses medication for the CE. Cost savings under the 340B program result from discounts given by drug manufacturers, who offer reduced drug prices in order to participate in other government programs, such as drug reimbursement under Medicaid.

To benefit from the 340B program, CEs are required to follow stringent rules and regulations. For instance, to be a compliant eligible dispensation of medication and available for replenishment of the drug under the 340B program, the following conditions must be met: (1) the medication is dispensed to an outpatient of the CE; (2) the medication is dispensed in an eligible outpatient location, (3) the medication's 11-digit National Drug Code (NDC) at dispensation matches the NDC of the medication purchased from a distributor, (4) an eligible physician orders the dispensation, (5) the medication is provided for an eligible service, (6) data on the dispensation is tracked accurately and is available for auditing, and (7) the medication is dispensed to a patient for whom the covered entity maintains responsibility for care.

The ClinFin server 102 may process the patient LARs for determining whether the health care provider has complied with the drug discount program, and whether the health care provider has leveraged those benefits. For example, the provider may be eligible to re-purchase drugs that were used to treat patients at a cost below a wholesale price if the provider complies with the rules and regulations of a drug discount program.

In the 340B program, for example, the ClinFin server 102 may process the patient LAR to determine if a particular patient encounter complies with the 340B rules and regulations, and if yes, the ClinFin server 102 may determine whether the health care provider reordered its drugs using the 340B program. If the ClinFin server 102 determines that the health care provider did not reorder a dispensed drugs using the 340B program, the ClinFin server 102 may alert an administrator of the health care provider and may automatically communicate a credit message via a computer network to a drug distributor server seeking a credit for overpayment. For example, the health care provider may have purchased a drug at a wholesale price (e.g., wholesale acquisition cost (WAC)) when it was entitled to purchase the drug at a lower 340B price. The requested credit may be the difference between a wholesale price and the discounted price. The drug distributor server may coordinate with the ClinFin server 102, or other computer accounting system of the health care provider, to credit the provider's account.

In some examples, the ClinFin server 102 may determine a total credit amount a provider is eligible to receive, but has failed to as yet obtain, under the drug discount program, and present that information in a graphical user interface at a user device of an administrator of the provider. The user device may be, for example, a computer, a laptop, a smartphone, or other communication device. Thus, the ClinFin server 102 may assist an administrator in identifying that the provider is not properly leveraging the drug discount program, for improving the provider's procedures to better leverage the drug discount program.

The ClinFin server 102 may also use the patient LARs to monitor whether the health care provider is ordering and using approved items (e.g., product and/or drugs) when treating patients. In an example, the ClinFin server 102 may process the patient LARs to determine a metric indicating whether or not approved items are being used to treat patients. The ClinFin server 102 may process linkages in the patient LARs to identify a master file 304 providing item identifiers for items used to treat patients. The ClinFin server 102 may compare the item identifiers to an approved list of items to generate a metric indicating whether or not an item used to treat a patient during a particular patient encounter is on the approved list. The ClinFin server 102 may utilize the metric when recommending whether to reorder an item. If the item is on the approved list, the metric may indicate approval to reorder the item. If not on the approved list, the ClinFin server 102 may identify an equivalent item on the approved list and recommend ordering the equivalent item instead.

The ClinFin server 102 may also use the patient LARs to improve treatment of an individual currently under the hospital's care and in aggregate to improve overall hospital performance clinically and financially. In an example, the ClinFin server 102 may determine whether a patient's care has deviated from a hospital's or peer hospital's preferred practices, and may notify a prescribing physician or hospital administration about this deviation. To make this determination, the ClinFin server 102 may process a patient's LAR to compare the items used, or scheduled to be used, to treat a patient for a particular ailment (e.g., assigned a particular diagnosis, or DRG, code) during a particular patient encounter with a list of approved supply item(s) and/or drug(s) for treating the ailment. The ClinFin server 102 may identify any unapproved supply item(s) and/or drug(s) used to treat a patient, and any alternate and/or less expensive on the approved list that perform similarly. For example, the ClinFin server 102 may process the patient's LAR to determine that a patient has been prescribed a branded medication that is not on the approved list. The ClinFin server 102 may search a drug database for an equivalent drug that is on the approved list. In another example, the ClinFin server 102 may determine that a branded medication is on the approved list, and a cheaper equivalent medication is also on the approved list. In a further example, the ClinFin server 102 may process the patient's LAR to determine that a doctor has scheduled to implant a more expensive medical device (which may or may not be on the approved list) when a less expensive and similarly effective medical device is available.

In response to processing the patient's LAR, the ClinFin server 102 may make recommendations about which drug(s) and/or supply item(s) to use. For example, the ClinFin server 102 may recommend that a clinician utilize an approved supply item instead of an unapproved supply item. If multiple drugs/items are on the approved list, the ClinFin server 102 may process patient LARs to determine aggregated metrics for assisting the provider in selecting which drugs/items to use based on clinical and financial outcomes. As described below, the ClinFin server 102 may determine that, in some instances, use of a more expensive drug or supply item may result in a lower total cost of care for a healthcare provider and/or improved quality of care (e.g., better clinical outcome) for a patient.

To improve performance of a healthcare provider, the ClinFin server 102 may assess how treatment variability impacts patient care and finances of the provider. In an example, the ClinFin server 102 may assist in identifying how variability in treating a particular ailment impacts patient outcomes and financially impacts the health care provider. In an example, the ClinFin server 102 may identify patient LARs having a same diagnosis code (e.g., DRG code) to identify some or all patients that have been treated for a particular ailment. The ClinFin server 102 may process the identified patient LARs to identify similarities and differences in how each patient was treated for assessing how variability affects financial and patient outcomes.

For example, the ClinFin server 102 may determine how different treatment modalities impact clinical and financial outcomes when treating patients having a particular ailment. A treatment modality may be a combination of supply item(s) and/or drug(s) used to treat a patient for a particular ailment. For example, the ClinFin server 102 may process patients LARs to identify differences in how patients were treated for the same ailment. Example differences include using different supplies, different medications, different physical therapy, and the like. The ClinFin server 102 may classify the patient LARs into groups based on common use of items (e.g., supplies and/or drugs) during treatment. In some examples, the ClinFin server 102 may prompt an administrator to define the different treatment modalities if there is a particular difference of interest.

In an example, the ClinFin server 102 may process the patient LARs for patients that had a knee replacement to identify that only some patients were prescribed an expensive antibiotic and others were not. The ClinFin server 102 may determine a first aggregate metric (e.g., an average total cost of care) when treating patients using a first treatment modality (e.g., using the antibiotic) and a second aggregate metric (e.g., a total average cost of care) using a second treatment modality (e.g., without using the antibiotic). An aggregate metric may be a statistical measure (e.g., an average) of one or more of: drug costs per patient encounter, supply costs per patient encounter, and labor charges per patient encounter. The ClinFin server 102 may also process the patient LARs to determine the percentage of patients who required further treatment (e.g., subsequently developed an infection) for each group that did and did not receive the antibiotic. The ClinFin server 102 may compare the aggregate metric to determine which is the lowest. The ClinFin server 102 may help identify outcomes that may not be expected. In an example, the ClinFin server 102 may determine that it is actually cheaper to prophylactically administer an expensive antibiotic to all patients. In some instances a hospital cannot recoup additional costs for further treatments of patients who get an infection (e.g., if a patient has to be readmitted), and thus the ClinFin server 102 may determine that use of the expensive antibiotic provides a better financial and clinical outcome, on average, because it leads to significantly fewer post-operative infections and subsequent readmissions for which costs cannot be recouped. The ClinFin server 102 may also use any desired statistical metric for aggregating costs (e.g., for determining a total cost of care) such as, for example, an average.

The ClinFin server 102 may also seek to identify cost outliers and may identify the percentage of patient encounters that exceed the aggregate measure for a particular modality by at least a predetermined amount (e.g., exceed an average total cost of care by at least a predetermined percentage). The ClinFin server 102 may perform its calculations with and without outlier data.

The ClinFin server 102 may provide a recommendation of which treatment modality to use in subsequent treatments for patients that receive a particular diagnosis. In many instances there may be a relationship between clinical and financial outcomes. A better clinical outcome may often indicate that an effective treatment was provided, and thus a provider receives an adequate payment for providing its services. A worse clinical outcome may indicate that an ineffective or the wrong treatment was provided, and a provider may not be able to recoup all of its costs from the patient and/or an insurance company. In some instances, the ClinFin server 102 may highlight a treatment modality that provides at least one improved clinical outcomes for its patients compared to other modalities (e.g., modality that minimizes the number of readmissions). Clinical outcomes may be based on, for example, the number of days a patient is in a hospital or on a ventilator, the number of readmissions for the same ailment, and the like. In another example, the ClinFin server 102 may make suggestions or provide alternative approaches based on the treatment modality having a lowest average total cost of care. In another example, the ClinFin server 102 may select a treatment modality that provides at least one improved clinical outcome for its patients and minimizes the hospital's average total cost of care to treat a particular ailment. In further examples, the ClinFin server 102 may base its recommendation on demographic information (e.g., age, ethnicity, etc.) and/or lifestyle information (e.g., smoker). For example, the ClinFin server 102 may process patient LARs to determine that a first treatment modality provides better financial and clinical outcomes for non-smokers, but smokers respond better to a second treatment modality. Thus, the ClinFin server 102 may assist a hospital by recommending a treatment modality that simultaneously attempts to improve patient care and hospital profitability.

In some examples, the ClinFin server 102 may base inventory ordering decisions on the recommended treatment modality. In an example, the ClinFin server 102 may determine what item(s) (e.g., product(s) and/or drug(s)) constitute the selected treatment modality, and automatically order those item(s) from a supplier. For example, the ClinFin server 102 may determine current inventory levels and estimate the number of treatments to be performed in a predetermined amount of time (e.g., average 20 knee replacements per month), and automatically communicate an order message via a network (e.g., the Internet, computer network, etc.) for ordering the item(s) corresponding to the selected treatment modality. For example, the ClinFin server 102 may determine that a healthcare provider performs, on average, 20 knee replacements in a predetermined time frame (e.g., per month). The ClinFin server 102 may determine what item(s) are associated with a recommended treatment modality, and may maintain sufficient supply in inventory to meet expected demand. A computer of the supplier may receive the order message and utilize a human and/or an automated robotic system to fulfill the order. The order may then be shipped to the health care provider or other desired location.

In some examples, the ClinFin server 102 may assign an urgency level to an order. Example urgency levels may include routine, expedited, and next day. Devices of workers at a supplier warehouse may include shipment software applications. Example worker devices include tablet computers, smart phones, computers, and the like. In response to receiving an order message, the shipment software application may activate a worker device to display a GUI with the order, its urgency level. In some instances, receipt of an order message may cause the shipment software application to establish a network connection to ClinFin server 102 to receive additional data on an order (e.g., if an order is associated with a higher urgency level). The ClinFin server 102 may also coordinate with the shipment software application of the worker device to route the order message to multiple devices associated with different workers that may fulfill the order, particularly if an order has a higher urgency level.

The ClinFin server 102 may also control ordering of product inventory to correct deviations between a clinician's prescribed items and approved items. In a further example, the ClinFin server 102 may control ordering of product inventory to correct deviations between a clinician's prescribed drug/supply and a recommended treatment modality. For instance, the ClinFin server 102 may automatically order from a supplier and/or cause shipment of a generic mediation and/or cheaper medical device to a physician for the time a procedure is to be completed that is consistent with a recommended treatment modality. In other examples, the ClinFin server 102 may notify the physician prior to the scheduled time to permit a mediation process to occur to enable the physician to justify why an unapproved item/drug should be used instead of an approved item/drug.

Figure 4:
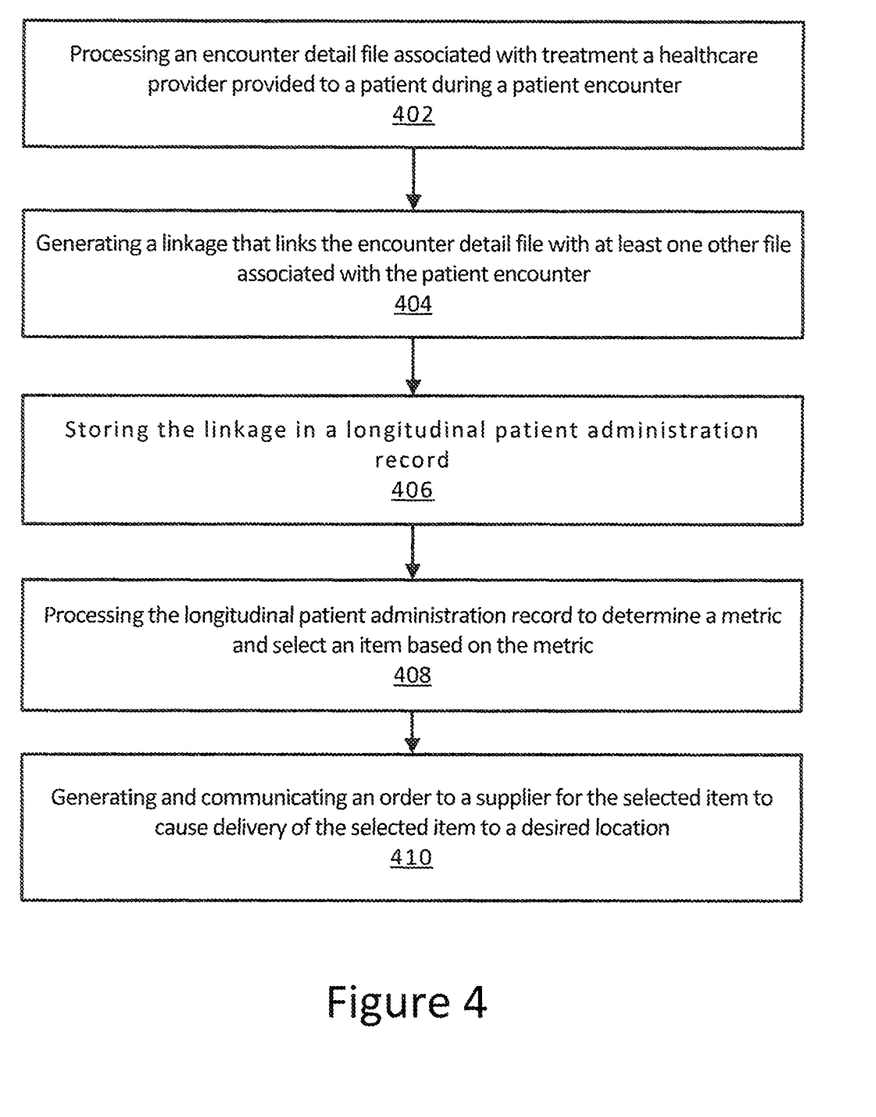
FIG. 4 illustrates a flow diagram of a method in accordance with example embodiments.

FIG. 4 illustrates a flow diagram of a method in accordance with example embodiments. The flow diagram may be implemented by a system or apparatus, such as, for example, ClinFin server 102. In some examples, one or more engines of the ClinFin server 102 may perform the process described in the flow diagram. Each of the blocks shown in the flow diagram may be repeated one or more times, one or more of the blocks may be modified, and one or more of the blocks may be omitted. The method may be stored on a non-transitory computer readable medium as computer executable instructions. The computer executable instructions, when executed by at least one processor, may cause the at least one processor, or at least one computer or other device, to perform the blocks as steps of a method one or more times. The flow diagram may begin at block 402.

In block 402, the method may include processing an encounter detail file associated with treatment a healthcare provider provided to a patient during a patient encounter. In an example, the ClinFin server 102 may receive a data feed from a hospital and/or from a supplier comprising an encounter detail file that identifies an item used to treat a patient during a particular patient encounter.

In block 404, the method may include generating a linkage that links the encounter detail file with at least one other file associated with the patient encounter. For example, the ClinFin server 102 may link the encounter detail file with one or more of a master file, a medical record file, and a transaction file associated with the particular patient encounter. The ClinFin server 102 may process the encounter detail file to determine what other files are associated with the same patient encounter, and link those files. The ClinFin server 102 may, for example, retrieve a utilization proxy from the encounter detail file. The ClinFin server 102 may search a database of master files to find a master file having the same utilization proxy as the encounter detail file. The ClinFin server 102 may then process the master file to identify its item detail. The ClinFin server 102 may search a database of medical records to identify a medical record having the same item detail as the master file and may search a database of transaction files to identify a transaction file having the same item detail as the master file. The encounter detail files, master files, medical record files, and transaction files may be stored in a common database or in multiple databases. In some examples, the ClinFin server 102 may apply validation criteria to the medical record file and the transaction file.

In block 406, the method may include storing a linkage in a longitudinal patient administration record. In an example, the ClinFin server 102 may generate and store a linkage for associating and/or retrieving each of the files associated with a particular patient encounter. In an example, a linkage may include the utilization proxy and the item detail. In another example, a linkage may include identifiers for each of the encounter detail file, the master file, the medical record file, and the transaction file identified in block 404. In further examples, the longitudinal patient administration record may create a linkage by storing the data from each of the encounter detail file 302, the master file 304, the medical record file 306, and the transaction file 308. In addition to storing the linkage in the LAR, the ClinFin server 102 may with time/date stamps and event entries as the health care provider provides treatment to the patient as part of the patient encounter. Each event entry may be associated with one or more of a drug cost, a supply cost, and/or a labor cost.

In block 408, the method may include processing the longitudinal patient administration record to determine a metric and select a drug or supply item based on the metric. In an example, a metric may indicate whether an item (e.g., product and/or drug) utilized in a patient encounter is on an approved list of items. The ClinFin server 102 may process the longitudinal patient administration record to generate a metric for each item indicating whether each item used during the patient encounter is on an approved list. If an approved item was used, the ClinFin server 102 may determine a current inventory level for the approved item and recommend reordering the approved item (e.g., when the inventory level drops below a predetermined level). In another example, the metric indicate that an unapproved item was used during the patient encounter. The ClinFin server 102 may identify an equivalent item on the approved list, and recommend reordering the equivalent item instead. In another example, a metric may be a statistical measure of a clinical or financial outcome for a patient encounter. For instance, the ClinFin server 102 may process multiple longitudinal patient administration records for recommending a particular one of multiple treatment modalities based on a financial and/or clinical outcome, and may order drug(s) and/or supply item(s) specified by the recommended treatment modality.

In block 410, the method may include generating and communicating an order to a supplier for the selected drug or supply item to cause delivery of the selected drug or supply item to a desired location. In an example, the ClinFin server 102 may check a current inventory level for the selected drug or supply item, and automatically order the selected drug or supply item from a supplier (e.g., if the inventory level falls below a particular level). For example, the ClinFin server 102 may communicate the order to a server or computer system of a supplier, which may fulfill the order. The ordered item/drug may also be delivered to any desired location.

The method of FIG. 4 may end, may repeat one or more times, or may return to any of the preceding blocks.

The example embodiments may provide a number of technical solutions to technical challenges. To date, existing software systems have failed to link disparate clinical and financial transaction data at the patient encounter level. Because of this failure, existing software systems are unable to determine how treatment variability impacts clinical and financial outcomes at the patient encounter level. The example embodiments may provide a technical solution to this technical challenge by creating linkages between multiple files for tying drug, supply, and labor costs to a particular patient encounter. Because of these linkages, the example embodiments may permit data-driven analysis of different treatment modalities to determine which modality provides better clinical and financial outcomes for a healthcare provider and its patients. Moreover, the example embodiments may support inventory management by automatically ordering items such that a health care provider has those items in inventory to meet expected demand.

The example embodiments may be implemented on computers and servers such as, for example, general purpose computers that may have, among other elements, a microprocessor (such as from the Intel Corporation, AMD or Motorola); volatile and non-volatile memory; one or more mass storage devices (i.e., a hard drive); various user input devices, such as a mouse, a keyboard, or a microphone; and a video display system. The computers and servers in FIG. 1 may be running on any one of many operating systems including, but not limited to WINDOWS, UNIX, LINUX, MAC OS, or Windows (XP, VISTA, etc.). It is contemplated, however, that any suitable operating system may be used for the present invention. The computers and servers in FIG. 1 may be a cluster of web servers, which may each be LINUX based and supported by a load balancer that decides which of the cluster of web servers should process a request based upon the current request-load of the available server(s).

The computers and servers may be connected via networks, including the Internet, WAN, LAN, Wi-Fi, other computer networks (now known or invented in the future), and/or any combination of the foregoing. It should be understood by those of ordinary skill in the art having the present specification, drawings, and claims before them that networks may connect the various components over any combination of wired and wireless conduits, including copper, fiber optic, microwaves, and other forms of radio frequency, electrical and/or optical communication techniques. It should also be understood that any network may be connected to any other network in a different manner. The interconnections between computers and servers in system 100 are examples. Any device may communicate with any other device via one or more networks.

The example embodiments may include additional devices and networks beyond those disclosed. Further, the functionality described as being performed by one device may be distributed and performed by two or more devices. Multiple devices may also be combined into a single device, which may perform the functionality of the combined devices.

The various participants and elements described herein may operate one or more computer apparatuses to facilitate the functions described herein. Any of the elements in the above-described Figures, including any servers, user terminals, or databases, may use any suitable number of subsystems to facilitate the functions described herein.

Any of the software components or functions described in this application, may be implemented as software code or computer readable instructions that may be executed by at least one processor using any suitable computer language such as, for example, Java, C++, or Perl using, for example, conventional or object-oriented techniques.

The software code may be stored as a series of instructions or commands on a non-transitory computer readable medium, such as a random access memory (RAM), a read only memory (ROM), a magnetic medium such as a hard-drive or a floppy disk, or an optical medium such as a CD-ROM. Any such computer readable medium may reside on or within a single computational apparatus and may be present on or within different computational apparatuses within a system or network.

It may be understood that the present invention as described above can be implemented in the form of control logic using computer software in a modular or integrated manner. Based on the disclosure and teachings provided herein, a person of ordinary skill in the art may know and appreciate other ways and/or methods to implement the present invention using hardware, software, or a combination of hardware and software.

The above description is illustrative and is not restrictive. Many variations of the invention will become apparent to those skilled in the art upon review of the disclosure. The scope of the invention should, therefore, be determined not with reference to the above description, but instead should be determined with reference to the pending claims along with their full scope or equivalents.

One or more features from any embodiment may be combined with one or more features of any other embodiment without departing from the scope of the invention. A recitation of "a", "an" or "the" is intended to mean "one or more" unless specifically indicated to the contrary. Recitation of "and/or" is intended to represent the most inclusive sense of the term unless specifically indicated to the contrary.

One or more of the elements of the present system may be claimed as means for accomplishing a particular function. Where such means-plus-function elements are used to describe certain elements of a claimed system it will be understood by those of ordinary skill in the art having the present specification, figures and claims before them, that the corresponding structure is a general purpose computer, processor, or microprocessor (as the case may be) programmed to perform the particularly recited function using functionality found in any general purpose computer without special programming and/or by implementing one or more algorithms to achieve the recited functionality. As would be understood by those of ordinary skill in the art that algorithm may be expressed within this disclosure as a mathematical formula, a flow chart, a narrative, and/or in any other manner that provides sufficient structure for those of ordinary skill in the art to implement the recited process and its equivalents.

While the present disclosure may be embodied in many different forms, the drawings and discussion are presented with the understanding that the present disclosure is an exemplification of the principles of one or more inventions and is not intended to limit any one of the inventions to the embodiments illustrated.

The present disclosure provides a solution to the long-felt need described above. In particular, systems and methods described herein may be configured to improve management of health care service providers. Further advantages and modifications of the above described system and method will readily occur to those skilled in the art. The disclosure, in its broader aspects, is therefore not limited to the specific details, representative system and methods, and illustrative examples shown and described above. Various modifications and variations can be made to the above specification without departing from the scope or spirit of the present disclosure, and it is intended that the present disclosure covers all such modifications and variations provided they come within the scope of the following claims and their equivalents.

What is claimed:

1. A computer-implemented method for securely linking together patient treatment data in a first format with health care provider data in a plurality of data standards for a treatment that a healthcare provider provided to a plurality of patients for an ailment during a patient encounter for each patient to enable data-driven evaluation of the financial and medical effectiveness of that treatment, the method comprising:

receiving, via a computer network by an engine comprising a first processor and a first memory storing first computer-executable instructions, an encounter detail file associated with the treatment that the healthcare provider provided to the patient during the patient encounter, wherein the encounter detail file includes the health care provider data in a plurality of data standards;

determining, by the engine, a unique identifier corresponding to the healthcare provider data of the encounter detail file;

retrieving, by the engine, event data, time/date stamp data, and utilization proxy from the encounter detail file based on the unique identifier, wherein the event data and time/date stamp data from the encounter detail file are in one or more of the plurality of data standards that are different from the encounter detail file;

updating, by the engine, a Longitudinal Patient Administration Record (LAR) database with the retrieved event data and time/date stamp data from the encounter detail file;

linking, by the engine, the LAR and a master file via the utilization proxy from the encounter detail file;

determining, by the engine, that the master file indicates cost and revenue data for an item was utilized in the patient encounter corresponding to the encounter detail file, wherein the item includes one or more of a supply item and a drug item and the master file includes cost and revenue data for the item and is maintained by a system that is separate from the engine, the system including a second processor and a second memory;

in response to determining, by the engine, that the master file indicates the item was utilized in the patient encounter corresponding to the encounter detail file, automatically sending, by the engine, a plurality of control signals to the system that is separate from the engine, the plurality of control signals causing the second processor to execute second computer-executable instructions stored in the second memory, the second computer-executable instructions including:

generating, by the engine, a first linkage between the master file and the encounter detail file, the first linkage indicating that the item specified in the encounter detail file was used in the patient encounter, generating, by the engine, a second linkage between an electronic medical record for the patient and a plurality of transaction files for other patient encounters that each have the item in common with the electronic medical record, wherein the plurality of transaction files each include the cost and revenue data for the item, updating, via the computer network and by the engine, the master file at the system with the first linkage, and updating, via the computer network and by the engine, the LAR at the system with both the first linkage and the second linkage;

determining, by the engine, a metric based on the LAR and the master file using the first linkage and the second linkage, wherein the metric indicates whether the item is on an approved list for the treatment the healthcare provider provided to the patient during the patient encounter and is a statistical measure of a clinical outcome for the patient encounter that used the item;

selecting, by the engine, the item for use during a further patient encounter based on the metric;

comparing, by the engine, the selected item to the approved list of items for the treatment that the healthcare provider provided to the patient during the patient encounter;

identifying, by the engine, an equivalent item for the selected item from the comparing step based on the metric; and generating and communicating, via the computer network and by the engine, an order to a supplier for the equivalent item to cause delivery of the equivalent item to a desired location to effect the treatment.

2. The method of claim 1, wherein the metric is based on at least one of a supply cost, a drug cost, and a labor cost for the treatment provided during the patient encounter.

3. The method of claim 1, wherein the LAR is one of a plurality of longitudinal patient administration records stored in a database.

4. The method of claim 3, further comprising:
processing the plurality of longitudinal patient administration records to identify a first treatment modality and a second treatment modality, wherein determining the metric includes:
determining a first aggregate metric for patient encounters that use the first treatment modality;
determining a second aggregate metric for patient encounters that use the second treatment modality;
comparing the first and the second aggregate metrics; and
recommending one of the first treatment modality and the second treatment modality based on the comparison.

5. The method of claim 3, further comprising processing a first of the plurality of longitudinal patient administration records to determine that a dispensed drug is eligible to be refilled using a drug discount program.

6. The method of claim 5, further comprising:
determining that the dispensed drug has been reordered and that the reorder was not in accordance with the drug discount program; and
generating and communicating a credit message to a distributor server requesting credit based on a difference between a purchase price of the dispensed drug and a discounted price available under the drug discount program.

7. The method of claim 1, wherein the order activates software operating on a worker device associated with the supplier causing the worker device to display the order and to establish a network connection.

8. An apparatus for securely linking together patient treatment data and in a first format with health care provider data in a plurality of data standards for a treatment that a healthcare provider provided to a plurality of patients for an ailment during a patient encounter for each patient to enable data-driven evaluation of the financial and medical effectiveness of that treatment, the apparatus comprising:
an engine including a first processor and a first memory storing first computer-executable instructions that, when executed by the first processor, cause the first processor to perform at least:
receiving an encounter detail file associated with the treatment that the healthcare provider provided to the patient during the patient encounter, wherein the encounter detail file includes the health care provider data in a plurality of data standards;
determining, by the engine, a unique identifier corresponding to the healthcare provider data of the encounter detail file;
retrieving, by the engine, event data, time/date stamp data, and a utilization proxy from the encounter detail file based on the unique identifier, wherein the event data and time/date stamp data from the encounter detail file are in one or more of the plurality of data standards that are different from the encounter detail file;
updating, by the engine, a Longitudinal Patient Administration Record (LAR) database with the retrieved event data and time/date stamp data from the encounter detail file;
linking, by the engine, the LAR and a master file via the utilization proxy from the encounter detail file;
determining that the master file indicates cost and revenue data for an item was utilized in the patient encounter corresponding to the encounter detail file, wherein the item includes one or more of a supply item and a drug item and the master file includes cost and revenue data for the item and is maintained by a system that is separate from the engine; and
in response to determining that the master file indicates the item was utilized in the patient encounter corresponding to the encounter detail file, automatically sending a plurality of control signals that link the encounter detail file with at least one other file associated with the patient encounter wherein, the system that is separate from the engine includes a second processor and a second memory storing second computer-executable instructions that, when executed by the second processor, cause the second processor to perform at least:
receiving the plurality of control signals from the engine at the system, the plurality of control signals causing the second processor to execute second computer-executable instructions stored in the second memory including:
generating, by the engine, a first linkage between the master file and the encounter detail file, the first linkage indicating that the item specified in the encounter detail file was used in the patient encounter,
generating, by the engine, a second linkage between an electronic medical record for the patient and a plurality of transaction files for other patient encounters that each have the item in common with the electronic medical record, wherein the plurality of transaction files each include the cost and revenue data for the item,
updating, via the computer network, the master file at the system with the first linkage, and
updating the LAR with both the first linkage and the second linkage;
wherein, in response to the system storing the linkages in a longitudinal patient administration record, the engine executes further first computer-executable instructions that, when executed by the first processor, cause the first processor to perform at least:
determining a metric based on the LAR and the master file using the first linkage and the second linkage, wherein the metric indicates whether the item is on an approved list for the treatment the healthcare provider provided to the patient during the patient encounter and is a statistical measure of a clinical outcome for the patient encounter that used the item;
selecting the item for use during a patient encounter based on the metric;
comparing the selected item to an approved list of items for the patient encounter the treatment that the healthcare provider provided to the patient during the patient encounter;
identifying an equivalent item for the selected item from the comparing step; and
generating and communicating, via the computer network, an order to a supplier for the equivalent item to cause delivery of the equivalent item to a desired location to effect the treatment.

9. The apparatus of claim 8, wherein the metric is based on at least one of a supply cost, a drug cost, and a labor cost for the treatment provided during the patient encounter.

10. The apparatus of claim 8, wherein the LAR is one of a plurality of longitudinal patient administration records stored in a database.

11. The apparatus of claim 10, wherein the computer-executable instructions, when executed by the at least one processor, further cause the apparatus at least to perform:
processing the plurality of longitudinal patient administration records to identify a first treatment modality and a second treatment modality, wherein determining the metric includes:
determining a first aggregate metric for patient encounters that use the first treatment modality;
determining a second aggregate metric for patient encounters that use the second treatment modality;
comparing the first and the second aggregate metrics; and
recommending one of the first treatment modality and the second treatment modality based on the comparison.

12. The apparatus of claim 10, wherein the computer-executable instructions, when executed by the at least one processor, further cause the apparatus at least to perform processing a first of the plurality of longitudinal patient administration records to determine that a dispensed drug is eligible to be refilled using a drug discount program.

13. The apparatus of claim 12, wherein the computer-executable instructions, when executed by the at least one processor, further cause the apparatus at least to perform:
determining that the dispensed drug has been reordered and that the reorder was not in accordance with the drug discount program; and
generating and communicating a credit message to a distributor server requesting credit based on a difference between a purchase price of the dispensed drug and a discounted price available under the drug discount program.

14. The apparatus of claim 8, wherein the order activates software operating on a worker device associated with the supplier causing the worker device to display the order and to establish a network connection.

15. A non-transitory computer readable medium storing computer-executable instructions for securely linking together patient treatment data in a first format with health care provider data in a plurality of data standards for a treatment that a healthcare provider provided to a plurality of patients for an ailment during a patient encounter for each patient to enable data-driven evaluation of the financial and medical effectiveness of that treatment, the instructions, when executed, cause at least one processor to perform at least:
receiving, via a computer network by an engine comprising a first processor and a first memory storing first computer-executable instructions, an encounter detail file associated with the treatment that the healthcare provider provided to the patient during the patient encounter, wherein the encounter detail file includes the health care provider data in a plurality of data standards;
determining, by the engine, a unique identifier corresponding to the healthcare provider data of the encounter detail file;
retrieving, by the engine, event data, time/date stamp data, and a utilization proxy from the encounter detail file based on the unique identifier, wherein the event data and time/date stamp data from the encounter detail file are in one or more of the plurality of data standards that are different from the encounter detail file;
updating, by the engine, a Longitudinal Patient Administration Record (LAR) database with the retrieved event data and time/date stamp data from the encounter detail file;
linking, by the engine, the LAR and a master file via the utilization proxy from the encounter detail file;
determining, by the engine, that the master file indicates cost and revenue data for an item was utilized in the patient encounter corresponding to the encounter detail file, wherein the item includes one or more of a supply item and a drug item and the master file includes cost and revenue data for the item and is maintained by a system that is separate from the engine, the system including a second processor and a second memory;
in response to determining, by the engine, that the master file indicates the item was utilized in the patient encounter corresponding to the encounter detail file, automatically sending, by the engine, a plurality of control signals to the system that is separate from the engine, the plurality of control signals causing the second processor to execute second computer-executable instructions stored in the second memory, the second computer-executable instructions including:
generating, by the engine, a first linkage between the master file and the encounter detail file, the first linkage indicating that the item specified in the encounter detail file was used in the patient encounter,
generating, by the engine, a second linkage between an electronic medical record for the patient and a plurality of transaction files for other patient encounters that each have the item in common with the electronic medical record, wherein the plurality of transaction files each include the cost and revenue data for the item,
updating, via the computer network and by the engine, the master file at the system with the first linkage, and
updating, via the computer network and by the engine, the LAR at the system with both the first linkage and the second linkage;
determining, by the engine, a metric based on the LAR and the master file using the first linkage and the second linkage,
wherein the metric indicates whether the item is on an approved list for the treatment the healthcare provider provided to the patient during the patient encounter and is a statistical measure of a clinical outcome for the patient encounter that used the item;
selecting, by the engine, the item for use during a further patient encounter based on the metric;
comparing, by the engine, the selected item to the approved list of items for the treatment that the healthcare provider provided to the patient during the patient encounter;
identifying, by the engine, an equivalent item for the selected item from the comparing step based on the metric; and
generating and communicating, via the computer network and by the engine, an order to a supplier for the equivalent item to cause delivery of the equivalent item to a desired location to effect the treatment.

16. The computer readable medium of claim 15, wherein the metric is based on at least one of a supply cost, a drug cost, and a labor cost for the treatment provided during the patient encounter.

17. The computer readable medium of claim 15, wherein the longitudinal patient administration record is one of a plurality of longitudinal patient administration records stored in a database.

18. The computer readable medium of claim 17, wherein the computer-executable instructions, when executed by the at least one processor, further cause the apparatus at least to perform:
- processing the plurality of longitudinal patient administration records to identify a first treatment modality and a second treatment modality, and the instructions further cause the processor to perform at least:
- determining a first aggregate metric for patient encounters that use the first treatment modality;
- determining a second aggregate metric for patient encounters that use the second treatment modality;
- comparing the first and the second aggregate metrics; and
- recommending one of the first treatment modality and the second treatment modality based on the comparison.

19. The computer readable medium of claim 17, wherein the computer-executable instructions, when executed by the at least one processor, further cause the apparatus at least to perform:
- processing a first of the plurality of longitudinal patient administration records to determine that a dispensed drug is eligible to be refilled using a drug discount program;
- determining that the dispensed drug has been reordered and that the reorder was not in accordance with the drug discount program; and
- generating and communicating a credit message to a distributor server requesting credit based on a difference between a purchase price of the dispensed drug and a discounted price available under the drug discount program.

20. The computer readable medium of claim 15, wherein the order activates software operating on a worker device associated with the supplier causing the worker device to display the order and to establish a network connection.

* * * * *